US006280991B1

(12) United States Patent
Raines

(10) Patent No.: US 6,280,991 B1
(45) Date of Patent: *Aug. 28, 2001

(54) ENGINEERED CYTOTOXIC RIBONCLEASE

(75) Inventor: Ronald T. Raines, Madison, WI (US)

(73) Assignee: Wisconsin Alumni Research Foundation, Madison, WI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/199,242

(22) Filed: Nov. 24, 1998

Related U.S. Application Data

(63) Continuation-in-part of application No. 08/950,866, filed on Oct. 15, 1997, now Pat. No. 5,840,296.
(60) Provisional application No. 60/097,797, filed on Aug. 25, 1998.

(51) Int. Cl.[7] .............................. C12N 9/22; A61K 38/46
(52) U.S. Cl. ..................... 435/199; 435/196; 435/183; 424/94.6; 935/10
(58) Field of Search ..................................... 435/199, 196, 435/183; 424/94.6; 935/10

(56) References Cited

U.S. PATENT DOCUMENTS

| 5,389,537 | 2/1995 | Raines et al. .................... 435/199 |
| 5,840,840 | 11/1998 | Rybak et al. .................... 530/350 |

OTHER PUBLICATIONS

Messmore et al. Ribonuclease A: Revealing Structure–FunctionRelationships with SemiSynthesis, J. Am. Chem. Soc. 117(31):8057–8060, Aug. 9, 1995.*

Weitman et al. Distribution of the Folate Receptor GP38 in Normal and Malignant Cell Lines and Tissues, Cancer Res. 52:3396–3401, Jun. 15, 1992.*

Alfacell Corporation, Reports and Press Releases from Oct. 1994–Nov. 1996.

Boix, et al., "Role of the N Terminus in RNase A Homologues: Differences in Catalytic Activity, Ribonuclease Inhibitor Interaction and Cytotoxicity," J. Mol Biol. 257:992–1007 (1996).

Delmonte, "Novel Ribonuclease Shows Antitumor Activity in Pancreatic Cancer and Mesothelioma", Oncology Times 18 No. 6, 1996.

Kim et al., "Mechanism of Ribonuclease Cytotoxicity", J. Biol. Chem. 270 No. 52:31097–31102, 1995..

Kim et al., "Structural Basis for the Biological Activities of Bovine Seminal Ribonuclease", J. Biol. Chem. 270, No. 18:10525–10530, 1995.

Kobe and Deisenhofer, "A Structural Basis of the Interactions Between Leucine–Rich Repeats and Protein Ligands", 374, No. 9: 183–186, 1995.

Leland, et al., "Ribonuclease A variants with potent cytotoxic activity," Proc. Natl. Acad. Sci. USA 95:10407–10412 (1998).

Raines et al., "Replacing a Surface Loop Endows Ribonuclease A with Angiogenic Activity", J. Biol. Chem. 270, No. 29: 17180–17184, 1995.

Schein, "From Housekeeper to Microsurgeon: The Diagnostic and Therapeutic Potential of Ribonucleases", Nature Biotechnology 15: 529–536, 1997.

Schultz, et al., "Structure and stability of the P93G variant of ribonuclease A," Protein Science 7:1620–1625 (1998).

Sendak, et al., "Kinetic and Thermodynamic Studies of the Folding/Unfolding of a Tryptophan–Containing Mutant of Ribonuclease A," Biochemistry 35: 12978–12992 (1996).

* cited by examiner

*Primary Examiner*—Rebecca E. Prouty
*Assistant Examiner*—Richard Hutson
(74) *Attorney, Agent, or Firm*—Quarles & Brady LLP

(57) ABSTRACT

Modified ribonucleases belonging to the RNase A superfamily of ribonucleases is disclosed. Each modified ribonuclease has a steric hindrance moiety added to it in the loop region corresponding to amino acids 85–94 of bovine pancreatic RNase A. Such a modified ribonuclease has reduced binding affinity for ribonuclease inhibitor (RI), exhibits wild-type ribonuclease activity, and exhibits enhanced cytotoxicity toward tumor cells, relative to the wild-type ribonuclease.

10 Claims, No Drawings

ENGINEERED CYTOTOXIC RIBONCLEASE

CROSS-REFERENCE TO RELATED APPLICATIONS

This application is a continuation-in-part of application no. 08/950,866 filed Oct. 15, 1997, now U.S. Pat. No. 5,840,296. This application also claims priority from provisional application 60/097,797 filed Aug. 25, 1998.

STATEMENT REGARDING FEDERALLY SPONSORED RESEARCH OR DEVELOPMENT

This invention was made with government support through grant CA73808 awarded by the National Institutes of Health. The United States Government has certain rights in this invention.

BACKGROUND OF THE INVENTION

The development of new drugs has contributed to the progress that has been made in recent years in the treatment of various types of cancer. However, certain cancers are refractory to the chemotherapeutic agents that are currently in use. These malignancies tend to be particularly virulent and are associated with a high mortality rate. Most existing chemotherapeutic agents have undesirable side effects as well. Consequently, there is ongoing interest, both within the medical community and among the general population, in the development of novel chemotherapeutic agents for the treatment of malignant tumors and other types of cancer.

One naturally occurring ribonuclease isolated from the leopard frog (Rana pipiens) has shown antitumor activity in patients with advanced inoperable pancreatic cancer and malignant mesothelioma in PhaseI/II studies (Delmonte, *Oncology Times* Vol. 18, No. 8, August 1996). The antitumor activity of this ribonuclease (referred to as Onconase) has been examined in more than 350 patients with a variety of solid tumors and has been shown to have antitumor activity against metastatic pancreatic carcinoma, advanced metastatic breast cancer, and malignant mesothelioma. Onconase is now being used Phase III human clinical trials against pancreatic and liver cancer.

In general, Onconase appears to be relatively safe to use as a chemotherapeutic in humans. It does not cause any of the major toxicities associated with conventional cytotoxic drugs, such as myelosuppression, gastrointestinal toxicity, or mucositis. Approximately one third of patients treated with Onconase developed flu-like symptoms and Grade 3 arthralgia with or without peripheral edema. The most serious complication associated with administration of Onconase is decreased renal function, which was observed in Phase I dose-ranging trials. The decreased renal function was reversible upon dose reduction.

In addition to treating various types of cancers, ribonucleases may have utility in the treatment of persons infected with HIV. Noncytotoxic concentrations of Onconase have been reported to significantly inhibit HIV production in several human cell lines persistently infected with HIV.

The cytotoxicity of ribonucleases was first demonstrated in solid tumors injected with milligram quantities of bovine pancreatic ribonuclease A (RNase A; EC3.1.27.5) (Ledoux, L. *Nature* 176:36–37, 1955; Ledoux, L. *Nature* 175:258–259). Smaller doses were found to have no effect on the tumors (de Lamirande, *Nature* 192:52–54, 1961). A ribonuclease that is cytotoxic at low levels was discovered in bull seminal plasma (Floridi et al., *Ital. Biol Sper.* 43:32–36, 1967; Dostal et al., *J. Reprod. Fertil.* 33:263–274, 1973). A ribonuclease with even greater cytotoxicity was isolated from frog eggs (Ardelt et al., *J. Biol. Chem.* 266:245–251, 1991), and this ribonuclease is the one now being tested in clinical trials under the name Onconase.

Ribonucleases catalyze the degradation of RNA. It has been demonstrated that the ribonucleolytic activity of cytotoxic ribonucleases is required for cytotoxicity (Kim et al., *J. Biol. Chem.* 270:10525–10530, 1995; (Ardelt et al., *J. Biol. Chem.* 266:245–251, 1991). Although the cytotoxicity of ribonucleases requires ribonucleolytic activity, ribonucleolytic activity alone is not sufficient to explain differential cytotoxicities observed among ribonucleases. For example, the ribonucleolytic activity of RNase A is approximately 1000-fold greater than that of Onconase, but Onconase has much greater cytotoxicity than RNase A. Thus, other properties of the enzymes must account for this difference.

Vertebrate cells contain a ribonuclease inhibitor (RI) that protects the cells from the potentially lethal effects of ribonuclease. The RI is a 50-kDa cytosolic protein that binds to ribonucleases with varying affinity. For example, RI binds to members of the bovine pancreatic ribonuclease A (RNase A) superfamily of ribonucleases with inhibition constants that span ten orders of magnitude, with $K_i$s ranging from $10^{-6}$ to $10^{-16}$ The cytotoxicity of a ribonuclease appears to be inversely related to the strength of the interaction between RI and the ribonuclease. For example, RNase A, which binds RI with a high affinity ($K_i=10^{-14}$M) is not cytotoxic. In contrast, Onconase binds RI with relatively low affinity ($K_i \geq 10^{-6}$M).

Some natural ribonucleases do not bind to RI. Bovine seminal ribonuclease (BS-RNase) is 80Cr identical in amino acid sequence to RNase A, but unlike RNase A, BS-RNase exists in a dimeric form. It has been shown that the quaternary structure of BS-RNase prevents binding by RI, thereby allowing the enzyme to retain its ribonucleolytic activity in the presence of RI (Kim et al., *Biochem. J.* 308:547–550, 1995; Kim et al., *J. Biol. Chem.* 270:10525–10530, 1995; Kim et al., *J. Biol. Chem.* 270:31097–31102, 1995). Onconase, a 104 amino acid residue protein that shares a high degree of homology with RNase A, is nevertheless resistant to binding by RI. The RI-Onconase complex has a $K_d$ of $\geq 10^{-6}$ M (Boix et al., *J. Mol. Biol.* 257:992–1007, 1996), which is at least one hundred million times less than that of the RI-RNase A complex.

Thus, the key distinction between Onconase and RNase A that accounts for the differential cytotoxicity observed in these ribonucleases is that Onconase is resistant to inhibition by RI. Normal cells produce an RI that binds ribonucleases noncovalently with a 1:1 stoichiometry and inhibits ribonucleolytic activity. The lower binding affinity of Onconase for RI prevents effective inhibition of the ribonucleolytic activity. This is the best explanation for the observed fact that Onconase is cytotoxic while ribonuclease A is not.

Recent studies in which the plasma clearance and tissue distribution of Onconase and RNase A in mice were examined showed that at three hours after the injection of Onconase or RNase A, 57% of Onconase is found in the kidney, whereas only 0.9% of human pancreatic ribonuclease is found in the kidney (Sung, et al. *Cancer Res.* 56:4180, 1996). The decreased renal function observed in patients who receive Onconase may be a consequence of an inability to effectively clear the Onconase protein from the kidneys.

A preferred therapeutic ribonuclease would be a cytotoxic ribonuclease that can be cleared from the kidneys more readily than Onconase. A cytotoxic ribonuclease that is readily cleared from the kidneys would be less likely to cause renal toxicity. Because reduced renal function is dose-limiting for Onconase, a cytotoxic ribonuclease that does not interfere with renal function would potentially offer the advantage of greater flexibility in determining optimal dosages. A ribonuclease with lower toxicity could be administered at higher doses where indicated, e.g., for those cases in which increased dosages would afford a more effective treatment for particular types of cancers or for particular individuals.

The side effects experienced by participants in clinical trials of Onconase are symptoms that are commonly associated with immune reactions. It is reasonable to expect that a ribonuclease from a species more closely related to humans than is the leopard frog would be less likely to cause an immune reaction. Less likely still to evoke an immune response would be a human ribonuclease. The intensity of an immune reaction may also be greater when larger amounts of the immunogenic protein are administered. Therefore, a cytotoxic ribonuclease with a higher specific activity than that of Onconase may potentially be a more effective chemotherapeutic. It may be possible to achieve effective cytotoxicity with the administration of smaller amounts of protein, thereby reducing the incidence and severity of symptoms associated with an immune reaction.

New cytotoxic ribonucleases with antitumor activity are needed to enhance the spectrum of chemotherapeutics available for treatment of human cancers.

BRIEF SUMMARY OF THE INVENTION

It is an object of the present invention to provide a novel, cytotoxic, ribonuclease that has potential usefulness in the treatment of human disease.

It is an object of the present invention to provide a method for modifying the amino acid sequence of a wild-type ribonuclease to produce a novel, cytotoxic, ribonuclease.

The present invention is a ribonuclease having a modified amino acid sequence, wherein the modified ribonuclease retains its ribonucleolytic activity, and wherein the modified ribonuclease has a lower binding affinity for RI than that of the unmodified ribonuclease and retains wild-type ribonucleolytic activity.

The present invention is a method for modifying the amino acid sequence of a ribonuclease to produce a modified ribonuclease, wherein the modified ribonuclease retains its ribonucleolytic activity, and wherein the modified ribonuclease has a binding affinity for RI that is lower than that of the unmodified ribonuclease and retains wild-type ribonucleolytic activity.

The present invention is also a method for inhibiting the proliferation of cancer cells, comprising delivering to the cells an effective amount of a modified ribonuclease, wherein the modified ribonuclease has a binding affinity for RI that is lower than that of the unmodified ribonuclease and retains wild-type ribonucleolytic activity.

Other objects, advantages, and features of the present invention will become apparent after review of the specification, drawings, and claims.

BRIEF DESCRIPTION OF THE SEVERAL VIEWS OF THE DRAWINGS

Not applicable.

DETAILED DESCRIPTION OF THE INVENTION

The work described in this patent is based on a premise. The premise is that evading from binding to RI is a key factor in making a ribonuclease cytotoxic. Evasion from binding with RI can arise from unfavorable steric interactions between RI and a ribonuclease. Two atoms cannot occupy the same point in space. Accordingly, adding bulk to the ribonuclease at a point that would normally contact RI when the ribonuclease binds to RI enables the ribonuclease to evade RI.

Adding steric bulk to the ribonuclease can be accomplished in multiple ways. One way involves changing the amino acid residues of the protein to other natural amino acids. Some of the 20 natural amino acids are larger than others. To increase the steric bulk at the point of contact between RI and ribonuclease, smaller amino acids can be replaced with larger ones in the region of contact. In a similar manner, additional amino acids can be inserted into the protein in that region. In either event, the effect is to make the protein unable to bind to RI due to the steric hindrance of the added bulk in this region.

A second strategy to add steric bulk involves preferably also modifying amino acids and then adding covalently a steric hindrance moiety to the molecule. Such a moiety can also be added to a natural amino acid of the wild-type protein. It is preferred, however, that a modifiable amino acid be inserted into an appropriate position by site-directed mutagenesis so that the steric hindrance moiety can be added to the modified amino acid. Two amino acids that are often modified are lysine and cysteine. Lysine is the only natural amino acid with an amino group (—$NH_2$) on its side chain. Chemical reagents that react only with amino groups will modify only lysine side chains. Likewise, cysteine is the only natural amino acid with a sulfhydryl group (—SH) on its side chain. Chemical reagents that react only with sulfhydryl groups will modify only cysteine side chains. Cysteine (1.7% of all amino acid residues) occurs less frequently in proteins than does lysine (5.7% of all residues). Moreover, cysteine residues are frequently involved in disulfide bonds (—SS—), which do not react with modification reagents. So, to add steric bulk to a protein at a specific point, a favorable strategy is to use site-directed mutagenesis to replace an existing amino acid with a cysteine residue, and then to modify the sulfhydryl group of the new cysteine residue by a chemical reaction. This technique has been called "cysteine elaboration", and we have applied it previously to study catalysis by RNase A (Messmore et al. *J. Am. Chem. Soc.* 117: 8057–8060).

The steric hindrance moiety is selected so as to be a chemical entity of sufficient size to interfere with the binding of ribonuclease inhibitor to the ribonuclease. The steric hindrance moiety can be a protein or can be selected from any other type of organic molecule that can be covalently bound to a protein such as ribonuclease. It is an advantage if the steric hindrance moiety also has potential affinity for the target cells. For example, it has been observed that malignant cells have a particular affinity to uptake folic acid. As disclosed below, folic acid can be added to a ribonuclease to serve effectively as a steric hindrance moiety and it is possible that the folic acid can also assist in uptake of the cytotoxic ribonuclease by targeted cells. Other candidates for the steric hindrance moiety include peptide ligands that bind to receptor molecules on the surface of targeted cells. Other possible steric hindrance moieties include vitamins, and targeting molecules having particular affinities for targeted cells.

The choice of modification site is important. A loop of amino acid residues of RNase A has been identified that makes intimate contact with RI in the RI°RNase A complex. These residues are numbers 85–94 in the amino acid sequence for native RNase A. This site has been identified as a preferred site for adding steric bulk by changing the amino acid residues of RNase A to other natural amino acids. These residues are also a preferred site for adding steric bulk by chemical modification. Because chemical modification is a more versatile method of adding steric bulk than is changing amino acid residues because larger groups with diverse properties can be added.

The present invention is thus a modified engineered ribonuclease that has either or both of an amino acid sequence that differs in at least one amino acid residue from the amino acid sequence of the corresponding wild-type ribonuclease or an steric hindrance moiety added chemically to the protein. The ribonuclease is preferably a member of the RNase A superfamily of ribonucleases. The modified ribonuclease retains its ribonucleolytic activity, the binding affinity of the modified ribonuclease for ribonuclease inhibitor is decreased relative to the binding affinity of unmodified ribonuclease for ribonuclease inhibitor, and the modified ribonuclease exhibits increased cytotoxic activity.

Modifications to the amino acid sequence of bovine pancreatic ribonuclease A that occur in a loop region defined by amino acid residues 85–94 of the native RNase A amino acid sequence and which create such steric interference will produce modified ribonucleases having reduced binding affinity for RI, wild-type ribonucleolytic activity, and enhanced cytotoxicity. It is also anticipated described here that other covalently attached moieties or side chains, such as a saccharine side chain, attached to the protein in this region to provide steric inhibition will work as well.

It is expected that in addition to bovine pancreatic RNase A and human pancreatic ribonuclease (hpRNase), other members of the RNase A superfamily of ribonucleases can be used in the practice of the invention. It is expected that a modification to a ribonuclease other than bovine pancreatic RNase A that occurs in a loop region corresponding to amino acid residues 85 through 94 of bovine pancreatic RNase A will produce a ribonuclease having reduced affinity for RI, wild-type ribonucleolytic activity, and increased cytotoxicity. By "a loop region corresponding to amino acid residues 85 through 94 of bovine pancreatic RNase A" it is meant a loop having about 10–12 amino acid residues that is defined by disulfide bonds formed between two cysteine residues, wherein the loop region begins about 75–85 amino acid residues from the N-terminal end of the ribonuclease and which sequence by "best fit" amino acid sequence corresponds to residues 85 and 94 of bovine RNase A.

The RNase A superfamily of ribonucleases constitutes a group of homologous (i.e., evolutionarily related) proteins from many mammalian, avian, reptilian, and amphibian sources. These proteins have a similar fold of their polypeptide chains, and catalyze the cleavage of RNA. A description of this superfamily can be found in Beintema et al. *Ribonucleases: Structures and Functions* 1997 pp 245–269, which is hereby incorporated by reference.

There are five exemplary human homologs of bovine pancreatic ribonuclease A that are expected to be useful in the development of cytotoxic ribonucleases for use in the treatment of human disease. Each of these five homologs has a conserved loop region analogous to the 10-amino acid residue loop region of RNase A (Table 1).

TABLE 1

| Enzyme | Aligned Sequence | | | | | | | | | | | | | | Seq ID No. |
|---|---|---|---|---|---|---|---|---|---|---|---|---|---|---|---|
| bovine pancreatic | (C) | R | E | T | G | S | S | K | Y | P | N | (C) | | | 6 |
| ribonuclease A | 84 | 85 | 86 | 87 | 88 | 89 | 90 | 91 | 92 | 93 | 94 | 95 | | | |
| human pancreatic | (C) | R | L | T | N | G | S | R | Y | P | N | (C) | | | 7 |
| ribonuclease | 84 | 85 | 86 | 87 | 88 | 89 | 90 | 91 | 92 | 93 | 94 | 95 | | | |
| human angiogenin | (C) | K | L | H | G | G | S | P | W | P | P | (C) | | | 8 |
| | 82 | 83 | 84 | 85 | 86 | 87 | 88 | 89 | 90 | 91 | 92 | 93 | | | |
| human eosinophil | (C) | D | L | I | N | P | G | A | Q | N | I | S | N | (C) | 9 |
| cationic protein | 83 | 84 | 85 | 86 | 87 | 88 | 89 | 90 | 91 | 92 | 93 | 94 | 95 | 96 | |
| human eosinophil | (C) | N | L | T | T | P | S | P | Q | N | I | S | N | (C) | 10 |
| derived neurotoxin | 83 | 84 | 85 | 86 | 87 | 88 | 89 | 90 | 91 | 92 | 93 | 94 | 95 | 96 | |
| human | (C) | R | D | T | G | S | S | R | A | P | N | (C) | | | 11 |
| ribonuclease 4 | 81 | 82 | 83 | 84 | 85 | 86 | 87 | 88 | 89 | 90 | 91 | 92 | | | |

By "enhanced cytotoxicity" it is meant that the modified ribonuclease exhibits greater cytotoxicity than the corresponding unmodified ribonuclease. In the examples below, cytotoxicity was evaluated using the human erythroleukemia cell line K-562. It is anticipated that the modified ribonuclease of the present invention is cytotoxic against other tumor cells in addition to K-562 cells.

Inhibition of cell proliferation is determined by calculating the percentage of viable K-562 cells treated with the modified or unmodified ribonuclease, where 100% viability is considered to be the number of viable cells that were treated with a solution of phosphate-buffered saline (PBS).

Preferably, the modified ribonuclease reduces cell viability by at least about 10%. More preferably, the modified ribonuclease reduces cell viability by at least about 20%. Most preferably, the modified ribonuclease reduces cell viability by about 50%, or even as much as about 75%.

The present invention is also a method for inhibiting the proliferation of tumor cells comprising providing a modified cytotoxic ribonuclease and delivering an effective amount of the ribonuclease to the tumor cells.

By "effective amount" is meant that amount of ribonuclease needed to cause a significant reduction in the proliferation of the tumor cells.

RI binds RNase A noncovalently with a 1:1 stoichiometry. The three-dimensional structure of the complex between RI and RNase A has been determined to a resolution of 2.5 (R-factor 19.4%) (Kobe et al., *Nature* 374:183–186, 1995). This structure showed that 24 of the 124 amino acid residues of RNase A contacted RI. Some regions of RNase A that contact RI were found to be distinct from the catalytic site.

It is contemplated here that a steric hindrance moiety is added to a ribonuclease to hinder its binding to RI. The choice of the steric hindrance moiety is important. A successful steric hindrance moiety is likely to be one that adds enough steric bulk to interfere with binding to RI, but that does not interfere with the other properties of the ribonuclease. Even given these constraints there are a large number of possible modifications, because many chemical reactions can be done to cysteine residues or to other amino acids.

Another desirable feature in a the steric hindrance moiety is that enhance binding and up-take by target cells. Certain reagents are known to have this property. For example, conjugating the sugar lactose to human low density lipoprotein (LDL) increases the up-take of LDL by liver cells (Attie et al., *Proc. Natl. Acad. Sci. USA* 77: 5923–5927). Conjugating the B-vitamin folic acid to a variety of proteins (including RNase A) increases the binding and up-take of the proteins by a variety of cell types (Leamon and Low, *J. Biol. Chem.* 267: 24966–24971). In these modification experiments, conjugation was done in a random manner. In other words, the point of attachment was not specified. Rather, the reactions were between the modification reagents and one or more of the many lysine residues in the proteins.

In the example below, a derivative of folic acid was coupled to the 85–94 loop of residues in human pancreatic ribonuclease (hpRNase). Folic acid was chosen because it is a bulky reagent that is likely to interfere with RI binding. We also chose folic acid because it is likely to enhance binding and up-take by cells. Certain cancer cells are known to have receptors to assist the active uptake of folic acid.

folic acid

Another member of the ribonuclease superfamily is the protein known as angiogenin, which induces vascular formation. Angiogenin binds to RI and has a domain analogous to residues 85–94 of hpRNase. It might be advantageous to add to angiogenin a steric hindrance moiety of isosorbide dinitrate, which is a known vasodilator. This would be a dual purpose addition to angiogenin by both blocking inhibition by RI and inducing vasodilation int he affected region of the body.

EXAMPLE

A general method was designed to couple a bulky molecule to a specific residue of human pancreatic ribonuclease (hpRNase). The residue that we chose was cysteine, because of the reasons described above. The sulfhydryl group of a cysteine residue is an excellent nucleophile for attack on carbon. The bulky molecule that we chose was a bromoacetamido derivative of folic acid, which we call "bamfolate". The methylene carbon of the bromoacetamido group of bamfolate is an excellent electrophile for attack by a sulfhydryl group.

"bamfolate"

The general scheme for the construction of the folate~hpRNase conjugate is as follows, and is described in detail below.

DNA Mutagenesis

Modification of RNase A by site-directed mutagenesis was done by the method described in detail in U.S. Pat. No.

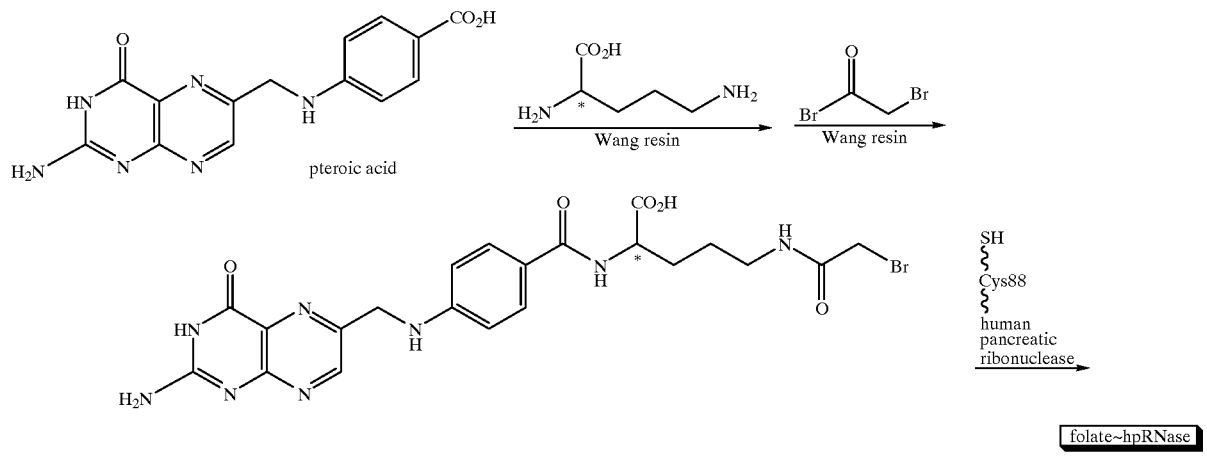

folate~hpRNase

Chemical Synthesis of Bamfolate

Folate derivatives are not readily soluble. Accordingly, our synthesis was done on a solid phase. Fmoc ornithine and Wang resin were from Novabiochem. Pteroic acid was from Sigma Chemical. All other chemicals were from Aldrich Chemical. All chemicals were used as received.

Wang resin (109 mg; 0.105 mmol; 0.96 mmol/g) and Fmoc ornithine (2.0 eq) were added to dimethylformamide (0.75 mL), and the resulting mixture was shaken for 15 minutes. Pyridine (28.4 µL; 3.3 eq) and 2,6-dichlorobenzoyl chloride (60 µL) was added, and the resulting mixture was shaken for 24 hours. The resin was then washed with dichloromethane. To benzoylate any remaining hydroxyl groups, a solution (2.0 mL) of dichloroethane containing pyridine (43 µL; 5.0 eq) and benzoyl chloride (43 µL) was added to the resin (Sieber *Tet. Lett.* 28: 6147–6150). The resulting mixture was shaken for 2 hours. The resin was isolated, and suspended in a solution (1.1 mL) of piperidine (20% v/v) in dimethylformamide. The resulting mixture was shaken for 15 minutes to remove the Fmoc group. The resin was then washed three times with dimethylformamide and three times with isopropanol.

Pteroic acid (32.8 mg) was slurried in dimethylformamide (1.9 mL). Isobutylchloroformate (10.3 µL; 1.0 eq) and triethylamine (14.7 µL; 1.0 eq) were added, and the resulting mixture was stirred for 30 minutes before being added to the resin. The resulting mixture was shaken for 5 hours, and was then washed with dichloromethane (Rosowsky et al. *Pteridines*, Vol 1, No. 2, pp 91–98).

The methyltrityl group was removed by washing with a solution of dichloromethane (95% v/v), triisopropylsilane (4% v/v), and trifluoroacetic acid (1% v/v).

The resin was suspended in dichloromethane (1.8 mL). N,N-Dimethylaniline (26.6 µL; 2 eq) and bromoacetylbromide (8.9 µL; 1.0 eq) were added, and the resulting mixture was shaken for 4 hours.

Bamfolate was removed from the resin by washing with a solution (2.0 mL) of trifluoroacetic acid (95% v/v), water (2.5% v/v), and triisopropylsilane (2.5% v/v), and dripping into ice-cold diethylether.

5,389,537, disclosure of which is hereby incorporated by reference. A cDNA that codes for human pancreatic ribonuclease (hpRNase) was expressed in a manner analogous to that used to express RNase A. Oligonucleotide-mediated site-directed mutagenesis (Kunkel et al., 1987) of the plasmid PHPR was used to generate an expression vector for modified hpRNase molecules having a specific amino acid substitution at a particular location, the modified hpRNase having an cysteine at residue 88 being designated N88C hpRNase. The oligonucleotide used to obtain N88C RNase is shown in SEQ ID NO:1, and codes for the reverse complement of residues 85 to 93 of N88C hpRNase Seq ID No. 2 sets forth the native coding sequence for hpRNase, while Seq ID No. 4 presents the coding sequence for N88C hpRNase.

Purification of the Protein Variant

Human pancreatic ribonuclease (hpRNase) is approximately 80% identical in amino acid sequence to RNase A. This level of identity suggests that the proteins have similar properties. Wild-type hpRNase and N88C hpRNase were purified essentially as described previously for RNase A, with the new cysteine residue at position 88 being protected from oxidation as described in Messmore et al. *J. Am. Chem. Soc.* 117: 8057–8060.

Coupling of Bamfolate to Protein Variant

Bamfolate was coupled to N88C hpRNase as described previously for the coupling of electrophiles to the sulfhydryl group of K41C RNase A (Messmore et al. *J. Am. Chem. Soc.* 117: 8057–8060).

Ribonucleolytic Activity

The ability of mutant ribonucleases to catalyze the cleavage of polymeric RNA was determined by UV spectroscopy, as described previously (delcardayre & Raines, *Biochemistry*, 33:6031–6037, 1994; delcardayre & Raines, *J. Mol. Biol.* 252:328–336, 1995).

Antitumor Aactivity Assay

The ribonuclease antitumor activity was evaluated as described previously (Kim, et al. *J. Biol. Chem.* 270:10525–10530, 1995). Onconase was included as a positive control and unmodified bovine pancreatic ribonuclease A was included as a negative control. The effect of various ribonucleases on the proliferation of human myeloid leukemia cell line K-562 (ATCC #CCL-243) was assessed as follows. Cells were maintained according to ATCC recommendations with the addition of antibiotics. Ribonuclease cytotoxicity toward K-562 cells was evaluated by measuring [$^3$H]-thymidine incorporation into newly synthesized DNA. Briefly, K-562 cells ($0.5 \times 10^4$ per well) were seeded into 96-well microtiterplates in 95- 1 volumes. Cells were cultivated in the presence of ribonucleases for 44 h, followed by a 4 h pulse with [$^3$H]-thymidine (0.2 Ci). Cells were then harvested onto glass fiber filters using a PHD cell harvester (Cambridge Technology, Inc.; Cambridge, Mass.) and lysed by passing several ml of water through the filters. DNA and other cellular macromolecules are retained by the filter, whereas small molecules, including unincorporated label, pass through the filters. After washing extensively with water, the filters were dried with methanol and counted using a liquid scintillation counter.

The incorporation of [$^3$H]-thymidine actually measures new DNA synthesis. Reduced incorporation of [$^3$H]-thymidine reflects cytostasis, rather than cell death. By other assays, however, Onconase has been shown to cause cell death (Wu et al., *J. Biol. Chem.* 268:10686–10695).

Binding Affinity for RI

The binding affinities of wild-type hpRNase and folate~hpRNase were assessed qualitatively by a gel-based assay (Wu et al., *J. Biol. Chem.* 268: 10686–10693).

Results

RI binds tightly to wild-type hpRNase, as expected by the similarity of hpRNase to RNase A. In contrast, RI does not bind tightly to folate~hpRNase, which remained catalytically active in the presence of RI.

Wild-type hpRNase was not toxic to human myeloid leukemia cell line K-562, whereas folate~hpRNase was more toxic than Onconase in inhibiting cellular proliferation. In particular, folate~hpRNase had and $IC_{50}$ value of 0.1 $\mu$M, whereas Onconase had an $IC_{50}$ value of 0.7 $\mu$M. These results show that residues 85–94 of a ribonuclease can be modified with a chemical group to confer cytotoxicity.

This result suggests that chemically modified ribonucleases with added steric hindrance moieties added can be superior to native ribonucleases in cytotoxicity.

What is claimed is:

1. An engineered cytotoxic ribonuclease comprising an amino acid sequence for a ribonuclease of the RNase A superfamily and a steric hindrance moiety covalently attached to an amino acid in the ribonuclease in a loop region functionally equivalent to the region of amino acid residues 85–94 of bovine pancreatic RNase A, the engineered ribonuclease having reduced binding affinity for ribonuclease inhibitor due to steric hindrance by the steric hindrance moiety, the modified ribonuclease retaining ribonucleolytic activity.

2. The ribonuclease of claim 1, wherein the modified ribonuclease is derived from human pancreatic ribonuclease.

3. The ribonuclease of claim 2, wherein the modified ribonuclease A is substituted at amino acid position 88 of the native sequence with a cysteine residue.

4. The ribonuclease of claim 1 wherein the steric hindrance moiety is a folic acid derivative.

5. The ribonuclease of claim 4 wherein the steric hindrance moiety is bamfolate.

6. A modified ribonuclease of the RNase A superfamily, the modified ribonuclease engineered by human modification thereof, the modified ribonuclease A having an alteration to its structure as compared to the corresponding wild-type ribonuclease, the alteration being the addition to the protein of a steric hindrance moiety, the steric hindrance moiety being covalently attached to an amino acid corresponding in position to amino acids 85–94 of RNase A, the steric hindrance moiety being sufficient in size to hinder binding to ribonuclease inhibitor while not interfering with ribonucleolytic activity.

7. A modified ribonuclease as claimed in claim 6 wherein the ribonuclease is human pancreatic ribonuclease.

8. A modified ribonuclease as claimed in claim 7 wherein the ribonuclease is modified from the native amino acid sequence by the substitution of a cysteine residue at amino acid position 88.

9. A modified ribonuclease as claimed in claim 6 wherein the steric hindrance moiety is a folic acid derivative.

10. A modified ribonuclease as claimed in claim 9 wherein the steric hindrance moiety is bamfolate.

* * * * *

SEQUENCE LISTING

<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:
      oligonucleotide for site-directed RNAse A
      mutagenesis at residue 88

<400> SEQUENCE: 1
cagactgaac gccaagagcc atggg                                          25

<210> SEQ ID NO 2
<211> LENGTH: 373
<212> TYPE: DNA
<213> ORGANISM: Homo sapiens
<220> FEATURE:
<221> NAME/KEY: CDS
<222> LOCATION: (1)..(372)

<400> SEQUENCE: 2 aaa gaa tct cgt gct aaa aaa ttc cag cgt cag cat atg gac tct gac      48
Lys Glu Ser Arg Ala Lys Lys Phe Gln Arg Gln His Met Asp Ser Asp
 1               5                  10                  15 tct tct ccg tct tct tct tct act tac tgc aac cag atg atg cgt cgt      96
Ser Ser Pro Ser Ser Ser Ser Thr Tyr Cys Asn Gln Met Met Arg Arg
            20                  25                  30 cgt aac atg act cag ggt cgt tgc aaa ccg gtt aac act ttc gtt cat     144
Arg Asn Met Thr Gln Gly Arg Cys Lys Pro Val Asn Thr Phe Val His
        35                  40                  45 gaa ccg ctg gtt gac gtt cag aac gtt tgc ttc cag gaa aaa gtt act     192
Glu Pro Leu Val Asp Val Gln Asn Val Cys Phe Gln Glu Lys Val Thr
    50                  55                  60 tgc aaa aac ggt cag ggt aac tgc tac aaa tct aac tct tct atg cat     240
Cys Lys Asn Gly Gln Gly Asn Cys Tyr Lys Ser Asn Ser Ser Met His
65                  70                  75                  80

```
atc act gac tgc cgt ctg act aac ggt tct cgt tac ccg aac tgc gct    288
Ile Thr Asp Cys Arg Leu Thr Asn Gly Ser Arg Tyr Pro Asn Cys Ala
                85                  90                  95 tac cgt act tct ccg aaa gaa cgt cat atc atc gtt gct tgc gaa ggt    336
Tyr Arg Thr Ser Pro Lys Glu Arg His Ile Ile Val Ala Cys Glu Gly
                100                 105                 110 tct ccg tac gtt ccg gtt cat ttc gac gct tct gtt g                  373
Ser Pro Tyr Val Pro Val His Phe Asp Ala Ser Val
            115                 120

<210> SEQ ID NO 3
<211> LENGTH: 124
<212> TYPE: PRT
<213> ORGANISM: Homo sapiens

<400> SEQUENCE: 3

Lys Glu Ser Arg Ala Lys Lys Phe Gln Arg Gln His Met Asp Ser Asp
 1               5                   10                  15

Ser Ser Pro Ser Ser Ser Ser Thr Tyr Cys Asn Gln Met Met Arg Arg
                20                  25                  30

Arg Asn Met Thr Gln Gly Arg Cys Lys Pro Val Asn Thr Phe Val His
            35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
                100                 105                 110

Ser Pro Tyr Val Pro Val His Phe Asp Ala Ser Val
            115                 120

<210> SEQ ID NO 4
<211> LENGTH: 373
<212> TYPE: DNA
<213> ORGANISM: Artificial Sequence
<220> FEATURE:
<223> OTHER INFORMATION: Description of Artificial Sequence: mutagenized
      RNAse A having cysteine at residue 88
<221> NAME/KEY: CDS
<222> LOCATION: (1)..(372)

<400> SEQUENCE: 4 aaa gaa tct cgt gct aaa aaa ttc cag cgt cag cat atg gac tct gac    48
Lys Glu Ser Arg Ala Lys Lys Phe Gln Arg Gln His Met Asp Ser Asp
 1               5                   10                  15 tct tct ccg tct tct tct tct act tac tgc aac cag atg atg cgt cgt    96
Ser Ser Pro Ser Ser Ser Ser Thr Tyr Cys Asn Gln Met Met Arg Arg
                20                  25                  30 cgt aac atg act cag ggt cgt tgc aaa ccg gtt aac act ttc gtt cat    144
Arg Asn Met Thr Gln Gly Arg Cys Lys Pro Val Asn Thr Phe Val His
            35                  40                  45 gaa ccg ctg gtt gac gtt cag aac gtt tgc ttc cag gaa aaa gtt act    192
Glu Pro Leu Val Asp Val Gln Asn Val Cys Phe Gln Glu Lys Val Thr
    50                  55                  60 tgc aaa aac ggt cag ggt aac tgc tac aaa tct aac tct tct atg cat    240
Cys Lys Asn Gly Gln Gly Asn Cys Tyr Lys Ser Asn Ser Ser Met His
65                  70                  75                  80 atc act gac tgc cgt ctg act cac ggt tct cgg tac ccg aac tgc gct    288
```

```
Ile Thr Asp Cys Arg Leu Thr His Gly Ser Arg Tyr Pro Asn Cys Ala
                85                  90                  95 tac cgt act tct ccg aaa gaa cgt cat atc atc gtt gct tgc gaa ggt         336
Tyr Arg Thr Ser Pro Lys Glu Arg His Ile Ile Val Ala Cys Glu Gly
            100                 105                 110 tct ccg tac gtt ccg gtt cat ttc gac gct tct gtt g                       373
Ser Pro Tyr Val Pro Val His Phe Asp Ala Ser Val
        115                 120

<210> SEQ ID NO 5
<211> LENGTH: 124
<212> TYPE: PRT
<213> ORGANISM: Artificial Sequence
<220> FEATURE:
<223> OTHER INFORMATION: Mutated sequence at residue 88

<400> SEQUENCE: 5

Lys Glu Ser Arg Ala Lys Lys Phe Gln Arg Gln His Met Asp Ser Asp
 1               5                  10                  15

Ser Ser Pro Ser Ser Ser Ser Thr Tyr Cys Asn Gln Met Met Arg Arg
            20                  25                  30

Arg Asn Met Thr Gln Gly Arg Cys Lys Pro Val Asn Thr Phe Val His
        35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr His Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val
        115                 120

<210> SEQ ID NO 6
<211> LENGTH: 10
<212> TYPE: PRT
<213> ORGANISM: Bovine
<220> FEATURE:
<223> OTHER INFORMATION: Partial sequence of Bovine RNAse A

<400> SEQUENCE: 6

Arg Glu Thr Gly Ser Ser Lys Tyr Pro Asn
 1               5                  10

<210> SEQ ID NO 7
<211> LENGTH: 10
<212> TYPE: PRT
<213> ORGANISM: Homo sapiens
<220> FEATURE:
<223> OTHER INFORMATION: Partial sequence of human pancreatic
      ribonuclease

<400> SEQUENCE: 7

Arg Leu Thr Asn Gly Ser Arg Tyr Pro Asn
 1               5                  10

<210> SEQ ID NO 8
<211> LENGTH: 10
<212> TYPE: PRT
<213> ORGANISM: Homo sapiens
<220> FEATURE:
<223> OTHER INFORMATION: Partial sequence of human angiogenin
```

-continued

```
<400> SEQUENCE: 8

Lys Leu His Gly Gly Ser Pro Trp Pro Pro
1               5                   10

<210> SEQ ID NO 9
<211> LENGTH: 12
<212> TYPE: PRT
<213> ORGANISM: Homo sapiens
<220> FEATURE:
<223> OTHER INFORMATION: Partial sequence from human eosinophil cationic
      protein

<400> SEQUENCE: 9

Asp Leu Ile Asn Pro Gly Ala Gln Asn Ile Ser Asn
1               5                   10

<210> SEQ ID NO 10
<211> LENGTH: 12
<212> TYPE: PRT
<213> ORGANISM: Homo sapiens
<220> FEATURE:
<223> OTHER INFORMATION: Partial sequence from human eosinophil derived
      neurotoxin

<400> SEQUENCE: 10

Asn Leu Thr Thr Pro Ser Pro Gln Asn Ile Ser Asn
1               5                   10

<210> SEQ ID NO 11
<211> LENGTH: 10
<212> TYPE: PRT
<213> ORGANISM: Homo sapiens
<220> FEATURE:
<223> OTHER INFORMATION: Partial sequence from human ribonuclease 4

<400> SEQUENCE: 11

Arg Asp Thr Gly Ser Ser Arg Ala Pro Asn
1               5                   10
```